US008921356B2

(12) United States Patent
Heldman

(10) Patent No.: US 8,921,356 B2
(45) Date of Patent: *Dec. 30, 2014

(54) COMPOSITIONS COMPRISING NICOTINIC AGONISTS AND METHODS OF USING SAME

(75) Inventor: Eliahu Heldman, Rehovot (IL)

(73) Assignee: NeuroDerm, Ltd., Rehovot (IL)

( * ) Notice: Subject to any disclaimer, the term of this patent is extended or adjusted under 35 U.S.C. 154(b) by 0 days.

This patent is subject to a terminal disclaimer.

(21) Appl. No.: 13/593,911

(22) Filed: Aug. 24, 2012

(65) Prior Publication Data

US 2013/0172321 A1    Jul. 4, 2013

Related U.S. Application Data

(63) Continuation of application No. 12/323,779, filed on Nov. 26, 2008, now Pat. No. 8,273,731.

(60) Provisional application No. 60/990,161, filed on Nov. 26, 2007.

(51) Int. Cl.
| | | |
|---|---|---|
| *A61K 31/55* | (2006.01) | |
| *A61K 31/465* | (2006.01) | |
| *A61K 31/167* | (2006.01) | |
| *A61K 31/27* | (2006.01) | |
| *A61K 31/4406* | (2006.01) | |

(52) U.S. Cl.
CPC .............. *A61K 31/55* (2013.01); *A61K 31/167* (2013.01); *A61K 31/27* (2013.01); *A61K 31/465* (2013.01); *A61K 31/4406* (2013.01)
USPC ........................... 514/217; 514/215; 514/343

(58) Field of Classification Search
None
See application file for complete search history.

(56) References Cited

U.S. PATENT DOCUMENTS

| | | | |
|---|---|---|---|
| 5,069,094 A | 12/1991 | Birkestrand | |
| 5,336,675 A | 8/1994 | Snorrason | |
| 5,656,286 A | 8/1997 | Miranda et al. | |
| 5,668,117 A | 9/1997 | Shapiro | |
| 6,043,224 A | 3/2000 | Lee et al. | |
| 6,187,756 B1 | 2/2001 | Lee et al. | |
| 6,852,741 B2 | 2/2005 | Papke | |
| 7,045,534 B2 | 5/2006 | Cooke et al. | |
| 7,214,381 B2 | 5/2007 | Carrara et al. | |
| 7,335,379 B2 | 2/2008 | Carrara et al. | |
| 7,390,821 B2 | 6/2008 | Cooke et al. | |
| 7,404,965 B2 | 7/2008 | Carrara et al. | |
| 8,273,731 B2 * | 9/2012 | Heldman | |
| 2003/0049308 A1 | 3/2003 | Theobald et al. | |
| 2003/0119879 A1 | 6/2003 | Landh et al. | |
| 2004/0167145 A1 | 8/2004 | Opitz et al. | |
| 2005/0014779 A1 | 1/2005 | Papke | |
| 2005/0191349 A1 | 9/2005 | Boehm et al. | |
| 2005/0234024 A1 | 10/2005 | Clarke | |
| 2007/0225379 A1 | 9/2007 | Carrara et al. | |
| 2008/0014252 A1 | 1/2008 | DelPrete | |
| 2010/0234349 A1 * | 9/2010 | Olsen et al. | |

FOREIGN PATENT DOCUMENTS

| | | |
|---|---|---|
| EP | 1468992 | 10/2004 |
| WO | WO-2005/115471 | 12/2005 |
| WO | WO-2008/0011484 A2 | 1/2008 |
| WO | WO-2009/069126 A1 | 6/2009 |

OTHER PUBLICATIONS

Rusted et al., Behavioural Brain Research, 2000, "Nicotinic treatment for degenerative neuropsychiatric disorders such as Alzheimer's disease and Parkinson's disease", vol. 113, pp. 121-129.*
Aarsland et al., International Journal of Geriatric Psychiatry, 2003, vol. 18, pp. 937-941.*
Biala et al. (2006) "Effects of Acute and Chronic Nicotine on Elevated Plus Maze in Mice: Involvement of Calcium Channels," *Life Sciences* 79(1):81-88.
Cohen et al. (1991) "Effects of Nicotine, Caffeine, and Their Combination on Locomotor Activity in Rats," *Pharmacology Biochemistry & Behavior* 40(1):121-123.
George et al. (2004) "Current Pharmacological Treatments for Nicotine Dependence," *Trends in Pharmacological Sciences* 25(1):42-48.
Giunta et al. (2004) "Galantamine and Nicotine Have a Synergistic Effect on Inhibition of Microglial Activation Induced by HIV-1 gp 120," *Brain Research Bulletin* 64(2):165-170.
Levin et al. (2005) "Nicotine and Clozapine Actions on Pre-Pulse Inhibition Deficits Caused by N-Methyl-D-Aspartate (NMDA) Glutamatergic Receptor Blockade," *Progress in Neuro-Psychophamacology & Biological Psychiatry* 29(4):581-586.
Martindale, The Complete Drug Reference, 33$^{rd}$ Edition, (2002) "Opipramol Hydrochloride," pp. 302.
Möller et al. (2001) "Opipramol for the Treatment of Generalized Anxiety Disorder: A Placebo-Controlled Trial Including an Alprazolam-Treated Group," *J. Clin. Psychopharmacol.* 21(1):59-65.
Müller et al. (2004) "Neuropharmacology of the Anxiolytic Drug Opripramol, a Sigma Site Ligand," *Pharmacopsychiatry* 37 Suppl. 3:S189-S197.

(Continued)

*Primary Examiner* — Savitha Rao
*Assistant Examiner* — Gregg Polansky
(74) *Attorney, Agent, or Firm* — Goodwin Procter LLP

(57) ABSTRACT

The disclosure is directed at least in part to compositions and methods comprising nicotinic agonists for treating e.g., nervous system disorders, in particular, to combination therapies that include a nicotinic agonist (for example, nicotine) and a nicotinic acetylcholine receptor desensitization inhibitor (for example, opipramol).

16 Claims, 11 Drawing Sheets

(56) References Cited

OTHER PUBLICATIONS

Perkins et al. (1994) "Acute Thermogenic Effects of Nicotine Combined with Caffeine During Light Physical Activity in Male and Female Smokers," *Am. J. Clin. Nutr* 60(3):312-319.

Perkins et al. (1994) "Subjective and Cardiovascular Responses to Nicotine Combined with Caffeine During Rest and Casual Activity," *Psychopharmacology* 113(3-4):438-444.

Prochazka et al. (2004) "A Randomized Trial of Nortriptyline Combined with Transdermal Nicotine for Smoking Cessation," *Arch Intern Med.* 164(20):2229.2233.

Rezvani et al. (2006) "Chronic Nicotine Interations with Clozapine and Risperidone and Attentional Function in Rats," *Progress in Neuro-Psychopharmacology & Biological Psychiatry* 30(2):190-197.

Trivedi et al. (1993) "Genotoxic Effects of Nicotine in Combination with Arecoline on CHO Cells," *Cancer Letters* 74(1-2):105-110.

van Eijk et al. (2001) "Reducing prescribing of highly anticholinergic antidepressants for elderly people: randomised trial of group versus individual academic detailing," *BMJ* 322:1-6.

Vazquez-Palacios et al. (2005) "Antidepressant Effects of Nicotine and Fluoxetine in an Animal Model of Depression Induced by Neonatal Treatment with Clomipramine," *Progress in Neuro-Psychopharmacology & Biological Psychiatry* 29(1):39-46.

EP Examination Report for Application No. 08 855 517.2 dated Mar. 8, 2012 (8 pages).

International Search Report, International Application No. PCT/IL2008/001546, mailed on Mar. 12, 2009 (60 pages).

Written Opinion of the International Searching Authority, International Application No. PCT/IL2008/001546, mailed on Mar. 12, 2009 (8 pages).

\* cited by examiner

COMPOSITIONS COMPRISING NICOTINIC AGONISTS AND METHODS OF USING SAME

RELATED APPLICATIONS

This application is a continuation of U.S. Ser. No. 12/323,779 filed Nov. 26, 2008, which claims priority to provisional application U.S. Ser. No. 60/990,161 filed Nov. 26, 2007, the entire disclosure of which is incorporated by reference herein.

FIELD

The present invention relates generally to compositions and methods of treating and/or controlling a disease, disorder or addiction responsive to the administration of a nicotinic agonist. At least in part, the invention relates, to compositions that include a nicotinic agonist and a nicotinic acetylcholine receptors (nAChRs) desensitization inhibitor.

BACKGROUND

Nicotinic ACh receptors (nAChRs) comprise a class of pentameric (containing five subunits) ligand-gated ion channels present in the central (CNS) and the peripheral (PNS) nervous systems as well as in the striated muscle. The nAChR of the nervous system and those found in peripheral neurons differ in structural (subunits composition) and functional aspects from nAChR found in striated muscles. Whereas the striated muscle receptors contain 2 $\alpha$ subunits ($\alpha$1) and one $\beta$ ($\beta$1), one $\gamma$ and one $\delta$ (or one $\epsilon$) subunits, the neuronal nAChR is composed of only $\alpha$ (at least two subunits among the $\alpha$2 to $\alpha$10 subtypes) and $\beta$ (generally three subunits among the $\beta$2 to $\beta$4 subtypes). The amino acid sequence for the $\alpha$ subunits of the neuronal nAChR ($\alpha$2 to $\alpha$10) consists of a glycolipid region (which contains the ACh binding site and four hydrophobic regions that span the membrane. The neuronal $\beta$ subunits ($\beta$2 to $\beta$4) do not have an adjacent pair of cystines, which are present in the $\alpha$ subunit ligand-binding region.

In general terms, two molecules of ACh binds to each of the $\alpha$-subunits of the receptor and induce a conformational change in all the receptor subunits, resulting in an opening of $Na^+/K^+$ channel, causing a local depolarization. The local depolarization may develop to an action potential, leading to physiological response such as muscle contraction when summed with the action of several receptors in the neuromuscular junction. Nicotinic receptors possess a relatively low affinity for ACh at rest. The affinity for acetylcholine is increased after the binding of the first ACh molecule (through an allosteric mechanism, which increases the likelihood of another molecule of ACh binding to the other $\alpha$ subunit). After prolonged exposure to ACh and at e.g., high concentrations of this neurotransmitter, the receptor channel may be closed in spite of an e.g., increase affinity of ACh to the receptor and the receptor subsequently can become desensitized.

An allosteric transition state model of the nAChR involves at least a resting state, an activated state and a "desensitized" closed channel state. Different nAChR ligands can differentially stabilize the conformational state to which they preferentially bind. For example, the agonists ACh and (−)-nicotine stabilize first the active state and then the desensitized state.

The nAChR is involved in the regulation of a variety of brain functions such as thermoregulation, cognition, attention etc. Thus, potentially, treatment with nicotine or drugs that directly or indirectly activate the nAChR may provide beneficial effects in alleviating cognitive dysfunctions such as dementia of Alzheimer's type, cognitive impairment associated with schizophrenia, attention deficit, e.g., in attention deficit hyperactivity disorder (ADHD). Nicotine has also been shown to be neuroprotective and a negative correlation between smoking and the development of neurodegenerative disorders such as Parkinson's disease and Alzheimer's disease has also been reported. In addition, nicotine is also used in cessation of smoking.

Over the past several years, a variety of research groups have focused on the development of selective nicotinic agonists. Nicotinic agonists may be useful in the treatment of a variety of neurological disorders including Alzheimer's disease, Parkinson's disease, and chronic pain. For example, nicotinic agonists such as epibatidine, epiboxidine, ABT-418, ABT-594, and SIB-1508 (altinicline) have been shown to exhibit analgesic properties suggesting that nAChR may be used as targets for novel analgesics.

The rapid desensitization of the nAChR may make nicotine, and other agents that activate directly or indirectly the nicotinic receptors, ineffective as therapeutic drugs. In addition, nicotinic agonists may be ineffective due to a process of uncompetitive blockade (open-channel block). Furthermore, prolonged activation appears to induce a long-lasting receptor inactivation. It would be desirable to find drugs that would retard desensitization of the receptor, thus prolonging the positive effect of nicotinic agonists or making them more effective during repeated administration.

SUMMARY

The present invention relates, in one aspect, to a pharmaceutical composition comprising a nicotinic agonist and a nAChR desensitization inhibitor, and a pharmaceutically acceptable carrier.

Any nicotinic agonist can be used in the compositions of the invention, such as, but not limited to, nicotine, nicotine metabolites, decamethonium bromide, epibatidine, lobeline, varenicline, epiboxidine, epiquinamide; ABT 418, i.e., (S)-3-methyl-5-(1-methyl-2-pyrrolidinyl) isoxazole, an isoxazole analog of (−)-nicotine that is an $\alpha 4\beta 2$ nAChR agonist; ABT-594, an azetidine derivative of epibatidine; ABT-894; DMXB-A, i.e., 3-(2,4-dimethoxybenzylidene)-anabaseine (also known as GTS-21), an $\alpha$7-nAChR selective agonist; SIB-1508 (altinicline); and RJR 2403 (metanicotine), and pharmaceutically acceptable salts and isomers thereof. Examples of active nicotine metabolites contemplated by the invention include cotinine, nornicotine, norcotinine, nicotine N-oxide, cotinine N-oxide, 3-hydroxy-cotinine, 5-hydroxy-cotinine and pharmaceutically acceptable salts thereof. Examples of nicotine salts include nicotine citrate and nicotine maleate. In a preferred embodiment, the nicotinic agonist is nicotine or a pharmaceutically acceptable salt or N-oxide thereof.

Exemplary nAChR desensitization inhibitors that can be used in the compositions of the invention include, but are not limited to, ion channel inhibitors, sodium channel inhibitors, potassium channel inhibitors, calcium channel inhibitors, beta blockers, sigma receptor antagonists, norepinephrine (NE) reuptake inhibitors, selective serotonin reuptake inhibitors, muscarinic agonists, adenosine antagonists, kappa-opioid agonists, dopamine and/or serotonin receptor antagonists, neurosteroids, sigma 1 receptor agonists, and acetylcholine esterase inhibitors.

Examples of ion channel inhibitors include lidocaine and mepivacaine; of sodium channel inhibitors include phenyloin, carbamazepine, lamotrigine, quinidine, procainamide, disopyramide, mexiletine, tocamide, flecamide, propafenone; of potassium channel inhibitors include nibetan, sotalol, amiodaraone, bretylium; of calcium channel inhibitors include verapamil, diltiazem; of beta blockers include propranolol, timolol, atenolol, metoprolol; of sigma receptor antagonists include opipramol, rimcazole; of NE reuptake inhibitors include dosulepin, lofepramine, nortriptyline, protriptyline; of selective serotonin reuptake inhibitors include clomipramine; of muscarinic agonists include McN-A-343, arecoline, cevimeline (AF-102B), AF-150, and AF-267B; of adenosine antagonists include caffeine; of kappa-opioid agonists include codeine or pentazocine; of dopamine and/or serotonin receptor antagonists include clozapine, DHA, or quetipine; of neurosteroids include alphaxolone, minaxolone; of sigma 1 receptor agonists include pentazocine). In preferred embodiments, the nAChR desensitization inhibitor may be selected from opipramol, McN-A-343, galantamine, lidocaine and clomipramine, or a pharmaceutically acceptable salts, ester or prodrug thereof. Other nAChR desensitization inhibitors may include trazodone, norfluoxetine, fluoxetine, or zimelidine.

In some embodiments, the pharmaceutical composition may include a nicotinic agonist and a nAChR desensitization inhibitor in a weight ratio of nicotinic agonist:nAChR desensitization inhibitor of about 1:2 to about 1:100, or about 1:5 to about 1:20, e.g. about 1:14.

Contemplated compositions of the invention may further comprise a pharmaceutically acceptable carrier. In an embodiment, the pharmaceutically acceptable carrier is suitable for transdermal or topical administration.

In preferred embodiments, the nicotinic agonist is nicotine, an isomer, pharmaceutically acceptable salt or N-oxide thereof, and the nAChR desensitization inhibitor is opipramol, McN-A-343, lidocaine, galantamine or clomipramine, or a pharmaceutically acceptable salt or prodrug thereof. In a more preferred embodiment, a pharmaceutical composition is provided that comprises: a) nicotine or a pharmaceutically acceptable salt or N-oxide thereof, and b) opipramol or a pharmaceutically acceptable salt, ester, or prodrug thereof.

Contemplated compositions of the invention may be suitable for any one of: oral, parenteral, transcutaneous, mucosal, transdermal or inhalation administration, and may be in the form of a chewing gum, sachet, thin film, transdermal patch, capsule, tablet, or nasal spray.

For example, provided herein is a transdermal patch comprising the composition comprising nicotine, opipramol and a pharmaceutically acceptable carrier suitable for transdermal or topical administration, wherein said carrier may comprise a skin penetration enhancer. Such a transdermal patch may be formulated to provide substantially continuous delivery of the nicotine and the opipramol to a patient.

Also provided herein is a controlled release composition for delivery of a composition comprising nicotine, opipramol and a pharmaceutically acceptable carrier which is capable of delivering the composition in a pre-determined delivery rate to a patient, for example wherein the pre-determined delivery rate is substantially continuously over at least 12 hours, or over at least 1 day, or over at least 3 days, or over at least 7 days (one week).

The pharmaceutical composition of the invention is useful for prevention or reduction of the transition of the nAChR to a "desensitized" closed channel state normally occurring after prolonged exposure to e.g., a nicotinic agonist. The compositions are useful for treatment of nervous system disorder, disease or condition such as CNS and PNS disorder, disease or condition. On one embodiment, the compositions are useful for treatment of cognitive dysfunction or cognitive disorders. In some other embodiments, the compositions are useful for treatment of CNS disorders including, but not limited to, anxiety, depression, Alzheimer's disease, Parkinson's disease, schizophrenia, attention deficit hyperactivity disorder (ADHD), attention deficit disorder (ADD), vascular dementia, Lewy body disease, post-traumatic dementia, Pick's disease, multiple sclerosis, Jakob-Creutzfeldt disease, drug addition such as nicotine addiction, alcohol addiction, *cannabis* addiction and cocaine addiction, obsessive disorders, compulsive disorders, impulse-control disorders, neurological conditions associated with acquired immune deficiency syndrome (AIDS), analegesia, and Huntington's disease In some other embodiments, the compositions are useful for treatment of PNS disorders including, but not limited to, neuropathies including mononeuropathies and polyneuropathies such as carpal tunnel syndrome, Guillain-Barre syndrome, facial palsy (or Bell's palsy), neuropathies caused by infectious agents, or diabetic, amyloid, and/or brachial plexus neuropathies, In one preferred embodiment, the composition of the invention is useful for treating or suppressing tobacco or nicotine dependence or usage, thus inducing smoking cessation.

Administration of a composition of the invention may provide for an effect of a subsequent administration of the nicotinic agonist to a patient that is substantially more therapeutically effective as compared to a subsequent administration of a nicotinic agonist using a method for treatment consisting of administering a nicotinic agonist alone. Additionally or separately, the disclosed compositions may provide for an effect of the nicotinic agonist that is substantially prolonged following said co-administration of the nAChR desensitization inhibitor as compared to administering to a patient a nicotinic agonist alone. For example, the effect of nicotinic agonist after co-administration of nAChR desensitization inhibitor may be about twice as effective as compared to administering to the patient the nicotinic agonist alone. In some embodiments, the nAChR desensitization inhibitor may reduce the desensitization of said nicotinic agonist for at least about 3 hours, at least about 12 hours, or at least about 1 day, at least about 3 days or more.

The nicotinic agonist and the nAChR desensitization inhibitor may be administered together in the same dosage form, or in separate dosage forms, e.g. different dosage forms. In some embodiments, the nicotinic agonist and the nAChR desensitization inhibitor may be administered sequentially or may be administered successively separated by about 10 minutes to about 4 hours, or about 10 minutes to about 12 hours, or 10 minutes to about 24 hours or more. Contemplated herein are embodiments wherein the nicotinic agonist and the nAChR desensitization inhibitor are each administered via a formulation chosen from: oral, parenteral, mucosal, inhalation and transdermal formulations, or a combination thereof, for example, the nicotinic agonist and the nAChR desensitization inhibitor may be co-administered in the form of chewing gum, sachets, thin film, transdermal patches, capsules, tablets, lozenges, or nasal sprays. For example, the nicotinic agonist may be administered transdermally, and the nAChR desensitization inhibitor may be administered orally or may be administered transdermally.

In some embodiments, the contemplated compositions include the nicotinic agonist and the nAChR desensitization inhibitor each administered in a substantially continuous manner over at least 12 hours, or over at least 1 day, or over at least three days, or over at least one week. For example, in one embodiment, the nicotinic agonist and the nAChR desensitization inhibitor may be administered in one transdermal patch. In another embodiment, the nicotinic agonist is delivered in a first transdermal patch and the nAChR desensitization inhibitor is administered in a second transdermal patch.

In accordance with the invention, the administration of the nicotinic agonist and the nAChR desensitization inhibitor may be repeated several times, e.g. within about 1 day, or about 2 days, of the previous administration of a contemplated co-therapy.

In some embodiments, the daily dosage may include about 5 mg/day to about 21 mg/day of nicotine and/or about 50 mg/day to about 150 mg/day, or about 50 mg to about 200 mg of opipramol. In this way, the nicotinic agonist may be effective for at least about 1 day, or at least about 3 days or more.

The invention further comprises a kit comprising: a) a pharmaceutical composition comprising a nicotinic agonist, preferably nicotine, an isomer, pharmaceutically acceptable salt or N-oxide thereof, b) a pharmaceutical composition comprising a nAChR desensitization inhibitor, preferably opipramol, a pharmaceutically acceptable salt, ester or prodrug thereof, and c) a leaflet with instructions for administration of said compositions for treatment of a CNS or PNS disease, disorder or condition and for induction of smoking cessation. In a preferred embodiment, the kit contains said compositions in the form of transdermal patches. For this purpose, also provided by the invention is a transdermal patch comprising opipramol.

In another aspect, the present invention provides a combination of a nicotinic agonist and a nAChR desensitization inhibitor for treatment of a CNS or PNS disease, disorder or condition or for induction of smoking cessation.

In a further aspect, the invention relates to the use of a combination of a nicotinic agonist and a nAChR desensitization inhibitor for the preparation of a pharmaceutical composition for treatment of a CNS or PNS disease, disorder or condition or for induction of smoking cessation.

In still another aspect, the invention relates to a method of prevention or reduction of the transition of the nAChR to a "desensitized" closed channel state normally occurring after prolonged exposure to e.g., a nicotinic agonist. In this aspect, the invention is directed to methods for treatment of nervous system disorder, such as a central nervous system disorder or a peripheral nervous system disorder as defined above, that includes co-administering to a patient in need thereof a therapeutically effective amount of a nicotinic agonist and a nAChR desensitization inhibitor.

BRIEF DESCRIPTION OF THE DRAWINGS

FIG. 3A: Each point is the Mean±S.E.M. of the change in body temperature compared to the temperature measured at time 0 (before the first injection) for at least five rats. FIG. 3B shows a bar histogram representing mean±S.E.M. of the maximum change in body temperature compared to the temperature measured just before the injection. D=day. Injection (Inj) of nicotine (filled circles), opipramol (triangles), and nicotine+opipramol (filled squares).

FIG. 4A: Each point is the Mean±S.E.M. of change in body temperature compared to the temperature measured at time 0 (before the first injection) for at least five rats. 4B Bar histogram representing mean±S.E.M. of the maximum change in body temperature compared to the temperature measured just before the injection.

DETAILED DESCRIPTION

Definitions

Figure 1:
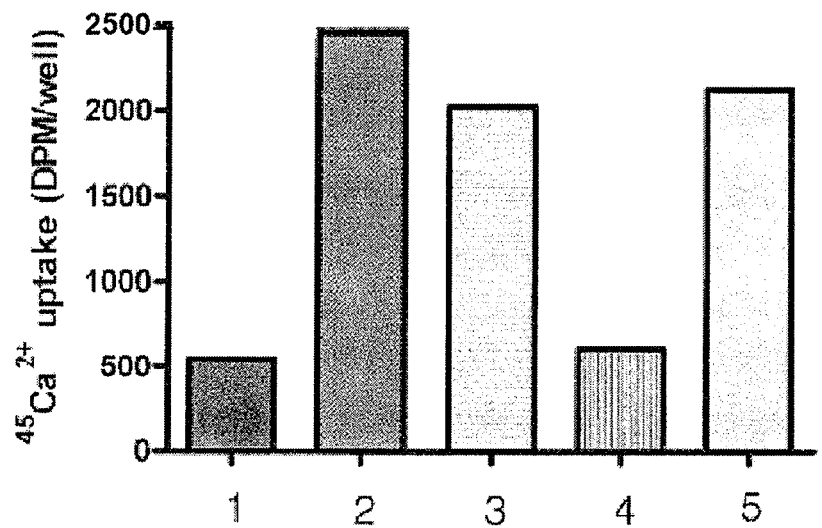
FIG. 1 depicts the effect of opipramol on nicotine-induced calcium uptake in human neuroblastoma cells treated with: 1. growth medium alone (DMEM) containing $^{45}Ca^{2+}$ (without any addition); 2. as 1 with 50 μM nicotine; 3. as 1 with 50 μM nicotine+10 μM opipramol; 4. as (2) but after incubating the cells for 15 min and treated with 50 μM nicotine+10 μM opipramol; and 5. as (2) but after preincubating the cells for 15 min and treated with 50 μM nicotine+10 μM opipramol. Radioactivity of intracellular $^{45}Ca^{2+}$ was measured after washing the cells with DMEM and expressed as disintegrations per minute (DPM).

For convenience, certain terms used in the specification, examples, and appended claims are collected in this section.

The term "carrier" refers to a diluent, adjuvant, excipient, or vehicle with which a contemplated agent or therapeutic is administered. The carriers in the pharmaceutical composition may comprise a binder, such as microcrystalline cellulose, polyvinylpyrrolidone (polyvidone or povidone), gum tragacanth, gelatin, starch, lactose or lactose monohydrate; a disintegrating agent, such as alginic acid, maize starch and the like; a lubricant or surfactant, such as magnesium stearate, or sodium lauryl sulphate; a glidant, such as colloidal silicon dioxide; a sweetening agent, such as sucrose or saccharin; and/or a flavoring agent, such as peppermint, methyl salicylate, or orange flavoring.

The phrase "combination therapy," as used herein, refers to co-administering a nicotinic agonist, for example, nicotine, and a nicotinic acetylcholine receptor desensitization inhibitor, e.g., opipramol, as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually weeks, months or years depending upon the combination selected). Combination therapy is intended to embrace administration of multiple therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single tablet or capsule having a fixed ratio of each therapeutic agent or in multiple, single capsules or tablets for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents, e.g. nicotinic agonists and nAChR desensitization inhibitor, can be administered by the same route or by different routes. For example, a first therapeutic agent of the combination selected may be administered transdermally while the other therapeutic agents of the combination may be administered orally. Alternatively, for example, both therapeutic agents may be administered orally or both may be administered transdermally.

Combination therapy can also embrace the administration of the therapeutic agents as described above in further combination with other biologically active ingredients and non-drug therapies. Where the combination therapy further comprises a non-drug treatment, the non-drug treatment may be conducted at any suitable time as long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The components of the combination may be administered to a patient simultaneously or sequentially. It will be appreciated that the components may be present in the same pharmaceutically acceptable carrier and, therefore, are administered simultaneously. Alternatively, the active ingredients may be present in separate pharmaceutical carriers, such as, conventional oral dosage forms, that can be administered either simultaneously or sequentially.

The term "continuously" as used herein refers to a drug delivered substantially slowly and substantially uninterrupted for e.g. 2, 3, 8, 12, or more hours or even 1, 2, 3, 5, 7 or 10 or more days. In some embodiments, the term continuously refers to delivery of a drug or agent that is substantially longer as compared to bolus single or multiple doses. For this purpose, the transdermal patches according to the invention are suitable.

The terms, "individual," "patient," or "subject" are used interchangeably herein and include any mammal, including animals, for example, primates, for example, humans, and other animals, for example, dogs, cats, swine, cattle, sheep, and horses. The compounds of the invention can be administered to a mammal, such as a human, but can also be other mammals, for example, an animal in need of veterinary treatment, for example, domestic animals (for example, dogs, cats, and the like), farm animals (for example, cows, sheep, pigs, horses, and the like) and laboratory animals (for example, rats, mice, guinea pigs, and the like).

The term "nicotinic agonist" refers to agents that at least partially bind and/or activate a nicotinic cholinergic receptor, including postganglionic nicotinic receptors, neuroeffector junctions in the peripheral nervous system, and/or at nicotinic receptors in the central nervous system. The term "nicotinic agonist" is meant to encompass nicotine and other compounds that substantially or at least partially bind a nicotine receptor and provide a pharmacological effect. The term encompasses the compounds described hereinabove. In addition, it also encompasses naturally-occurring compounds (including, but not limited to, small molecules, polypeptides, peptides, etc., particularly naturally-occurring plant alkaloids, and the like), endogenous ligands (e.g., purified from a natural source, recombinantly produced, or synthetic, and further including derivatives and variants of such endogenous ligands), and synthetically produced compounds (e.g., small molecules, peptides, etc.).

The term "indirect nicotinic agonist" refers to agents capable of increasing the level of Ach and thus activating the nAChR indirectly. Indirect nicotinic agonists may include reversible choline esterase inhibitors such as physostigmine, donepezil, tacrine, rivastigmine, pyridostigmine, neostigmine, and the like, and may include non-reversible choline esterase inhibitors such as echothiphate.

The term "nicotine" is intended to mean the naturally occurring alkaloid known as nicotine, having the chemical name S-3-(1-methyl-2-pyrrolidinyl)pyridine, which may be isolated and purified from nature or synthetically produced in any manner. This term is also intended to encompass nicotine metabolites and derivatives and like compounds, for example cotinine, norcotinine, nornicotine, nicotine N-oxide, cotinine N-oxide, 3-hydroxycotinine and 5-hydroxycotinine as well as pharmaceutically acceptable salts thereof e.g. commonly occurring salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate, ethanesulfonate, benzenesulfonate, p-toluene sulfonate, camphorate and pamoate salts, as well as N-oxides, esters or prodrugs thereof.

The term "nicotinic acetylcholine receptor desensitization inhibitor" or "nAChR desensitization inhibitor" refers to an agent that at least partially reduces, inhibits, or retards nicotinic acetylcholine receptor desensitization, for example at least partially reduces the desensitization caused by repeated (e.g. two or more doses) administration of nicotine to a patient. Such nAChR desensitization inhibitors may attenuate nAChR desensitization from a slight decrease to full inhibition (i.e. no apparent reduction in nicotinic action between the first application of a nicotinic agonist and consequent repeated applications of said agonist).

The term "therapeutically effective" refers to the ability of an active ingredient, alone or in combination with another active agent, to elicit the biological or medical response that is being sought by a researcher, veterinarian, medical doctor or other clinician.

The term "therapeutically effective amount" includes the amount of an active ingredient, or combination of active ingredients, that will elicit the biological or medical response that is being sought by the researcher, veterinarian, medical doctor or other clinician. The compounds of the invention are administered in amounts effective for treating a CNS or PNS disorder. Alternatively, a therapeutically effective amount of an active ingredient is the quantity of the compound required to achieve a desired therapeutic and/or prophylactic effect, such as the amount of the active ingredient that results in the prevention of or a decrease in the symptoms associated with the condition (for example, to meet an end-point).

The terms "cognitive disorder" or "cognitive dysfunction" refer to mental conditions that cause patients to have difficulty in thinking with symptoms generally marked by impaired attention, perception, reasoning, memory and judgment. One type of cognitive disorder is dementia, which is characterized by gradual impairment of multiple cognitive abilities including memory, language and judgement, Memory deficit and dementia states can be caused by, or associated with, neurodegenerative or neurological diseases, disorders or conditions such as Alzheimer's disease, Parkinson's disease, Huntington's disease, Lewy body disease, Pick's disease, Jakob-Creutzfeld disease, multiple sclerosis, anxiety, depression, schizophrenia, limbic encephalitis, normal pressure hydrocephalus, age-related memory impairment; brain damage caused by stroke, brain injuries and vascular dementia; infectious diseases such as neurosyphilis, acquired immune deficiency syndrome (AIDS), fungal infections, tuberculosis; drug intoxication such as alcohol, nicotine, *cannabis*, and cocaine addiction or heavy metal exposure. Attention deficit disorder (ADD) and attention deficit hyperactivity disorder (ADHD) are types of cognitive dysfunction found both in children and adults.

The term "treating" is used herein to denote treating the disease, disorder or condition, or ameliorating, alleviating, reducing, or suppressing symptoms of the disease, or slowing or stopping the progress of the disease. Thus, in some embodiments, administration of the composition or combination of the invention may ameliorate, alleviate or reduce the cognitive disorder symptoms in dementia associated with the diseases, disorders and conditions as mentioned above.

The terms "pharmaceutically acceptable" or "pharmacologically acceptable" refer to molecular entities and compositions that do not produce an adverse, allergic or other untoward reaction when administered to an animal, or to a human, as appropriate. The term, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

Pharmaceutically acceptable salts of the disclosed compounds can be synthesized, for example, from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile. Lists of suitable salts are found in Remington's Pharmaceutical Sciences, 20th ed., Lippincott Williams & Wilkins, Baltimore, Md., 2000, p. 704.

The term "prodrug" refers to compounds that are transformed in vivo to yield a disclosed compound or a pharmaceutically acceptable salt, hydrate or solvate of the compound. The transformation may occur by various mechanisms, such as through hydrolysis in blood. For example, if a nAChR desensitization inhibitor, or a pharmaceutically acceptable salt, hydrate or solvate of this compound contains a carboxylic acid functional group, a prodrug can comprise an ester formed by the replacement of the hydrogen atom of the acid group with a group such as ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyl-oxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-(C1-C2)alkyl and piperidino-, pyrrolidino- or morpholino($C_2$-$C_3$)alkyl.

Similarly, if a nicotinic agonist or nAChR desensitization inhibitor contains an alcohol functional group, a prodrug can be formed by the replacement of the hydrogen atom of the alcohol group with a group such as ($C_1$-$C_6$)alkanoyl-oxymethyl, 1-($C_1$-$C_6$)alkanoyloxy)ethyl, 1-methyl-1-($C_1$-$C_6$)alkanoyloxy) ethyl ($C_1$-$C_6$)alkoxycarbonyloxymethyl, N—($C_1$-$C_6$)alkoxycarbonylaminomethyl, succinoyl, ($C_1$-$C_6$)alkanoyl, α-amino($C_1$-$C_4$)alkanoyl, arylacyl and α-aminoacyl, or α-amino-acyl-α-aminoacyl, where each α-aminoacyl group is independently selected from the naturally occurring L-amino acids, $P(O)(OH)_2$, $—P(O)(O(C_1$-$C_6)$ alkyl$)_2$ or glycosyl (the radical resulting from the removal of a hydroxyl group of the hemiacetal form of a carbohydrate).

If a nAChR desensitization inhibitor or nicotinic agonist incorporates an amino functional group, a prodrug can be formed by the replacement of a hydrogen atom in the amino group with a group such as R-carbonyl, RO-carbonyl, NRR'-carbonyl where R and R' are each independently ($C_1$-$C_{10}$) alkyl, ($C_3$-$C_7$)cycloalkyl, benzyl, or R-carbonyl is a natural α-aminoacyl or natural α-aminoacyl-natural α-aminoacyl, —C(OH)C(O)$OY_1$ wherein $Y_1$ is H, ($C_1$-$C_6$)alkyl or benzyl, —C($OY_2$)$Y_3$ wherein $Y_2$ is ($C_1$-$C_4$)alkyl and $Y_3$ is ($C_1$-$C_6$) alkyl, carboxy($C_1$-$C_6$)alkyl, amino($C_1$-$C_4$)alkyl or mono-N— or di-N,N—($C_1$-$C_6$)alkylaminoalkyl, —C($Y_4$)$Y_5$ wherein $Y_4$ is H or methyl and $Y_5$ is mono-N— or di-N,N—($C_1$-$C_6$)alkylamino, morpholino, piperidin-1-yl or pyrrolidin-1-yl.

The term "transdermal delivery" refers to drug delivery across the skin, usually accomplished without breaking the skin.

Methods

Provided herein are methods of treating CNS and PNS diseases, disorders or conditions using disclosed compositions or formulations. In some embodiments, a disclosed method provides for an effect of a subsequent administration of a nicotinic agonist, after, e.g. a first administration of nicotinic agonist and nAChR desensitization inhibitor, to said patient is substantially more therapeutically effective as compared to, e.g. a subsequent administration of a nicotinic agonist, or a nicotinic agonist and a nAChR desensitization inhibitor using a method for treatment consisting of first administrating to said patient a nicotinic agonist alone. For example, in some embodiments, the nAChR desensitization inhibitor of the disclosed combination may reduce desensitization of an administered nicotinic agonist for at least about 3 hours, at least about 6 hours, at least about 12 hours, or at least about one, two, three days, or about 1 week or more.

Also provided herein are methods of treating CNS and PNS diseases such as those above, that may provide for an effect of a subsequent administration of an indirect nicotinic agonist, after e.g. a first administration of indirect nicotinic agonist and nAChR desensitization inhibitor.

In another embodiment, a method provides for substantially prolonged nicotinic agonist effect following said co-administering in said patient, for example, as compared to the nicotinic effect obtained by administering to a patient a nicotinic agonist alone. For example, the disclosed methods may provide a nicotinic agonist effect, after co-administration, that is about, e.g. 1.5 times, twice or even three times as effective or 1.5 times, twice, or even three times prolonged as compared to administering the nicotinic agonist alone.

Disclosed methods comprise, for example, a combination therapy, which can be achieved by co-administering to a patient a nicotinic agonist and a nAChR desensitization inhibitor. The nicotinic agonist and a nAChR desensitization inhibitor can be administered as a (i) single dosage form or composition, (ii) simultaneously as separate dosage forms or pharmaceutical compositions, (iii) sequentially, as separate dosage forms starting with the nicotinic agonist and then administering nAChR desensitization inhibitor, or starting with the nAChR desensitization inhibitor and then administering the nicotinic inhibitor, (iv) successively, separated by for example about 10 minutes to about 4 hours, about 1-4 hours, about 1-8 hours, about 1 hour to about 12 or 24 or more hours, or more or (v) individually followed by the combination. The methods disclosed herein may occur before, during, or after other dosing regimens that may include, for example nicotinic agonists, a nAChR desensitization inhibitor, and other agents e.g., for treating CNS or PNS diseases, disorders or conditions. In an embodiment, a disclosed methods may comprise a combination therapy, which can be achieved by co-administering to a patient an indirect nicotinic agonist and a nAChR desensitization inhibitor.

For example, a nAChR desensitization inhibitor, in some embodiments, may be administered prior to, concomitantly with, or shortly after, administration of the nicotinic agonist. In an embodiment, a nAChR desensitization inhibitor may be administered concomitantly with the nicotinic agonist, for example in the same composition. For example, in an embodiment, the nAChR desensitization inhibitor may be administered orally, and the nicotinic agonist is administered transdermally. For example, administration of nicotine may be less suitable for oral delivery because it may, for example, cause unacceptable adverse events, and/or may be absorbed from the gut into the portal blood and degrade promptly by the liver. In certain embodiments, however, the nAChR desensitization inhibitor can be administered with nicotinic agonist in dosage forms that deliver nicotinic agonist to the systemic circulation via absorption through mucosal membranes or the skin, including dosage forms such as chewing gum, thin films (e.g. orally dissolving thin films), sachets, transdermal patches, capsules, tablets, lozenges, nasal sprays and oral inhalation devices.

Alternatively, the nicotinic agonist and the nAChR desensitization inhibitor may be administered topically or transdermally (e.g. via a transdermal patch) to a patient. For example, the nAChR desensitization inhibitor and/or the nicotinic agonist may be administered to a patient substantially continuously, e.g. by transdermal patch and/or by a sustained release composition. For example, the nicotinic agonist and the nAChR desensitization inhibitor may be administered via one transdermal patch (e.g., substantially continuously), or the nicotinic agonist may be administered in a first transdermal patch and the nAChR desensitization inhibitor may be administered in a second transdermal patch, which is different than the first (e.g., both may be administered substantially continuously via two patches, or the first patch may have a different delivery rate than the second patch, and/or the first patch may have a different surface area as compared to the second patch). In an embodiment, a first patch may be placed at one location on a patient and the second patch may be placed at another location which may be substantially near the first patch or may be at a substantially different location.

In another embodiment, the nicotinic agonist and nAChR desensitization inhibitor may be administered to a patient in a substantially continuous manner, e.g., provide substantially steady amounts over 1 day, 3 days, 1 week, 10 days, or more. In another embodiment, disclosed methods may further comprise re-administering to the patient a therapeutically effective amount of a nicotinic agonist and an AChR desensitization inhibitor, for example, within about 12 hours, 1 day, 2 days or more, of the previous administration.

In some embodiments, the nicotinic agonist is administered in escalating doses. Such escalating doses may comprise a first dose level and a second dose level. In other embodiments, escalating doses may comprise at least a first dosage level, a second dosage level, and a third dosage level, and optionally a fourth, fifth, or sixth dosage level. The nicotinic acetylcholine receptor desensitization inhibitor may be provided in one dosage level when in administered in combination with a nicotinic agonist, or may be administered in escalating doses.

A first, second, third or more dosage levels can be administered to a patient for about 2 days to about 6 months or more in duration. For example, first, second and/or third dose levels are each administered to a subject for about 1 week to about 26 weeks, or about 1 week to about 12 weeks, or about 1 week to about four weeks. Alternatively, the first, second and/or third dosage levels are administered to a subject for about 2 days to about 40 days or to about 6 months.

The nicotinic agonist may be administered in a therapeutically effective amount. In some embodiments the contemplated therapeutically effective dosages of a nicotinic agonist, while not effective when used in monotherapy, may be effective when used in the combinations disclosed herein.

Exemplary methods contemplated herein and comprising administering to a patient a disclosed composition or dosage form or combination therapy include methods of treating Alzheimer's disease, Parkinson's disease, schizophrenia, attention deficit hyperactivity disorder (ADHD), attention deficit disorder (ADD), vascular dementia, Lewy body disease, post-traumatic dementia, Pick's disease, multiple sclerosis, Jakob-Creutzfeldt disease, nicotine addiction, alcohol addiction, *cannabis* addiction, cocaine addiction, obsessive disorders, compulsive disorders, impulse-control disorders, neurological conditions associated with acquired immune deficiency syndrome (AIDS), aging and/or Huntington's disease. In another embodiment, a method for managing and/or treating pain in a patient is provided. In some embodiments, a method of treating a cognitive disorder or dysfunction is contemplated, comprising administering to a patient a disclosed composition or dosage form, for example, a method of treating dementia, Alzheimer's disease, Parkinson's disease, schizophrenia, or nicotine or other addiction. In an embodiment, a method is also provided for treating and/or ameliorating mild cognitive impairment e.g. a patient in early stages of Alzheimer's disease.

The present invention, in some embodiments, provides a method for smoking cessation, comprising administering to a smoking individual a disclosed composition, e.g. a composition comprising nicotine and a compound capable of reducing the nAChR desensitization caused by the nicotine. In other embodiments, provided herein are methods for treating anxiety, depression, restless legs syndrome, Tourette's syndrome, chronic tic disorder, or essential tremor, comprising administering to a patient a disclosed composition or dosage form or combination therapy. A method is also provided for treating behavioral e.g. compulsive disorders, such as obsessive-compulsive disorder and/or generalized anxiety disorders.

Also disclosed is a method for slowing or ameliorating the progression of Parkinson's disease, for example, upon administration, the nicotinic agonist may act as a neuroprotective agent, wherein the neuroprotective effect may be enhanced by e.g. co-administration of a nAChR desensitization inhibitor.

In a particular embodiment, methods are disclosed that provide treating or suppressing tobacco or nicotine dependence or usage, said method comprising administering to a human a disclosed composition or dosage form or combination therapy. Also provided are methods of treating drug addiction, dependence or tolerance to stimulants such as nicotine, *cannabis* or cocaine, comprising administering to a patient a composition or dosage form or combination therapy.

Also provided herein are methods for increasing blood flow to ischemic tissue in patient, comprising administering a disclosed composition or dosage form or combination therapy effective to stimulate angiogenesis and increase blood flow to the ischemic tissue. Contemplated herein, in an embodiment, are methods for providing neuronal protection, e.g. from oxidative stress, or such methods may provide for e.g. delayed death of e.g. hippocampal neurons that may be e.g. ischemia induced. For example, in an embodiment, a method for treating and/or ameliorating stroke in a patient who is at risk of, or who has had a stroke or other vascular disease, is provided herein. Also provided herein are methods for treating and/or ameliorating diseases related to neuronal death (for example motor neuron death), e.g. amyotrophic lateral sclerosis.

Also provided herein are methods for treating peripheral nervous disorders such as carpal tunnel syndrome, Guillain-Barre syndrome, or diabetic, amyloid, and/or brachial plexus neuropathies, comprising administering disclosed compounds, co-therapies, and/or dosage forms.

For example, a method for increasing the efficacy of a nicotinic agonist by inhibiting or reducing the desensitization of nAChRs in an individual being treated with said nicotinic agonist is provided, which comprises co-administering to the individual a therapeutically effective amount of a compound capable of reducing the nAChR desensitization, thus increasing the efficacy of the nicotinic agonist.

Disclosed methods of e.g., treating a CNS or PNS disease, disorder or condition may, in some embodiments, further include administering a desensitization inhibitor of a receptor other than nAChR. In some embodiments, for example, such an inhibitor may be the same or different than the nAChR desensitization inhibitor contemplated herein.

In an exemplary embodiment, the nAChR desensitization inhibitor is a tricyclic antidepressant such as opipramol or imipramine, or a tetracyclic antidepressant such as galantamine (a tetracyclic alkaloid), an inhibitor of acetylcholine esterase, mirtazapine, or maprotiline. In another embodiment, the nAChR desensitization inhibitor is McN-A-343, a drug that may selectively activate certain subclasses of muscarinic receptors.

Compositions and Formulations

Compositions provided herein may include at least one nicotinic agonist, at least one nAChR desensitization inhibitor, and a pharmaceutically acceptable carrier. In an exemplary embodiment, a pharmaceutical composition comprises nicotine and opipramol, or its pharmaceutically acceptable salts, esters and/or prodrugs thereof. In other embodiments, the pharmaceutical composition may comprise nicotine and galantamine, clomipramine, lidocaine or McN-A-343.

In some embodiments, the disclosed compositions may include a nicotinic agonist (e.g. nicotine) and a nAChR desensitization inhibitor (e.g. opipramol) in a weight ratio of nicotinic agonist:nAChR desensitization inhibitor of about 1:100 to about 100:1, e.g., about 1:1 to about 1:50, about 1:1 to about 1:5, 1:5 to about 1:50, about 1:5 to about 1:20, or about 1:10 to about 1:15, e.g. about 1:14, or about 1:13.

The pharmaceutical compositions may be in any suitable form including forms for oral, parenteral, transcutaneous, mucosal, or inhalation administration. In some embodiments, the compositions may be administered in the form of chewing gum, sachets, transdermal patches, capsules, tablets, lozenges, or nasal sprays.

For topical administration, the disclosed compositions may be administered in the form of a gel, a cream, a paste, a lotion, a spray, a suspension, a powder, a dispersion, a salve and an ointment.

In some embodiments, the composition for transdermal delivery is a transdermal ointment, cream, gel, lotion or other transdermal solution or suspension. Preferably, for transdermal delivery, a transdermal patch can be used that may be a single layer drug in adhesive patch, a multi-layer drug in adhesive patch, a reservoir patch, a matrix patch, a microneedle patch or an iontophoretic patch, which typically requires applying a direct current. For example, a transdermal delivery system (patch) may be used, such as a transdermal nicotine delivery device described in U.S. Pat. No. 4,839,174. The compositions for transdermal delivery including the patches may include a skin penetration enhancer as known in the art. In still further embodiments, the transdermal patch is adapted for sustained release.

In certain embodiments, the disclosed compositions may be administered orally. For oral administration, the active ingredients may take the form of solid dose forms, for example, tablets (both swallowable and chewable forms), capsules or gel caps, prepared by conventional means with pharmaceutically acceptable excipients and carriers such as binding agents (e.g. pregelatinised maize starch, polyvinylpyrrolidone, hydroxypropylmethylcellulose and the like), fillers (e.g. lactose, microcrystalline cellulose, calcium phosphate and the like), lubricants (e.g. magnesium stearate, talc, silica and the like), disintegrating agents (e.g. potato starch, sodium starch glycollate and the like), wetting agents (e.g. sodium laurylsulphate) and the like. Such tablets may also be coated by methods well known in the art. Alternatively, a pharmaceutical preparation may be in liquid form, for example, solutions, syrups or suspensions, or may be presented as a drug product for reconstitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl p-hydroxybenzoates or sorbic acid).

The disclosed compositions may be administered as single or multiple doses in any suitable form as described above or they may be administered substantially continuously through a drug delivery device or a sustained release composition. For example, a sustained release composition may include such excipients as poly(lactide-co-glycolide) e.g., microparticles of PLGA; polyacrylate, latex, starch, cellulose, dextran and the like, supramolecular biovectors, which comprise a non-liquid hydrophilic core (e.g., a cross-linked polysaccharide or oligosaccharide) and, optionally, an external layer comprising an amphiphilic compound, such as a phospholipid (see e.g., U.S. Pat. No. 5,151,254, WO 94/20078, WO/94/23701 and WO 96/06638), biodegradable microspheres (e.g., polylactate polyglycolate) (see e.g. U.S. Pat. Nos. 4,897,268;

5,075,109; 5,928,647; 5,811,128; 5,820,883; 5,853,763; 5,814,344, 5,407,609 and 5,942,252.) and calcium phosphate core particles.

Contemplated dosages of a nicotinic agonist for use in the disclosed methods and compositions should be large enough to produce the desired effect, whereby, for example, desensitization of the nAChR is substantially prevented and the action of the nicotinic agonist is prolonged, and further, where the symptoms of the disease, disorder or condition are substantially reduced or ameliorated. The doses should not be so large as to cause adverse side effects. In some embodiments, a therapeutically effective amount of nicotinic agonist may range from 1 to 100 mg per patient. For example, nicotine may be administered at about 5 mg/day to about 21 mg/day, or about 10 mg/day to about 21 mg/day, or about 15 mg/day, 20 mg/day, or about 7 mg/day. In other embodiments, a nictonic agonist, e.g., nicotine is administered from about 0.05 mg/kg/day to about 5 mg/kg/day. In situations where a nicotinic agonist is administered continuously, the dosage may, in some embodiments, be kept in the lower ranges to avoid undesired side-effects.

Opipramol may be, for example, administered at dosage of about 50 mg or about 100 mg/day, e.g. about 10 mg/day to about 300 mg/day, about 50 mg/day to about 200 mg/day, about 50 mg/day to about 150 mg/day or about 50 mg/day to about 250 mg/day. For example, 200 mg/day, or 125 mg/day, 150 mg/day or 250 mg/day of opipramol may be administered. In another embodiment, opipramol may be administered from about 0.2 mg/kg/day to about 20 mg/kg/day.

In some embodiments, lidocaine may be administered from about 0.1 mg/kg/day to about 10 mg/kg/day. For example, a total dose for percutaneous administration may be about 5 to about 300 mg.

The present invention also relates to the use of a compound capable of reducing nAChR desensitization caused by a nicotinic agonist, for the preparation of a medicament comprising also a nicotinic agonist or for administration with a medicament comprising a nicotinic agonist, for treatment of a disease, disorder or condition responsive to the administration of a nicotinic agonist.

The present invention also provides for a package or kit for treatment of a disease, disorder or condition responsive to the administration of a nicotinic agonist, e.g., a CNS or PNS disease, disorder or condition, said kit comprising a pharmaceutical composition comprising a nicotinic agonist, a pharmaceutical composition comprising a nAChR desensitization inhibitor, and a leaflet with instructions for administration of said compositions for treatment of a disease, disorder or condition responsive to the administration of a nicotinic agonist.

The pharmaceutical compositions of the kit may be comprised each in one container and the kit will comprise two containers, a first container containing a nicotinic agonist and a pharmaceutically acceptable carrier and the second container containing a nAChR desensitization inhibitor and a pharmaceutically acceptable carrier, and the leaflet. The two pharmaceutical compositions may be in similar formulation form, for example, each is in the form of a transdermal patch, or in different formulation forms, for example, one is presented as a transdermal patch and the other is presented as oral form. For example, nicotine may be comprised within a transdermal patch and opipramol as tablets. In another embodiment, the kit includes a first dosage form, e.g. a transdermal patch, that includes a nicotinic agonist (e.g., nicotine), and a second dosage form, e.g. a transdermal patch that includes a nAChR desensitization inhibitor (e.g., opipramol), and instructions for use Also provided is controlled release medical device for delivery of a composition comprising a) nicotine, b) opipramol or pharmaceutically acceptable salts, esters, and prodrugs thereof; which is capable of delivering the composition in a pre-determined delivery rate to a patient. In one embodiment, the pre-determined delivery rate is substantially continuously over at least 1 day.

The examples that follow are intended in no way to limit the scope of this invention but are provided to illustrate the methods of the present invention. Many other embodiments of this invention will be apparent to one skilled in the art.

EXAMPLES

Materials and Methods (i) Cells—SK-N-SH human neuroblastoma cell line was obtained from the American Type Culture Collection (ATTC).

(ii) Animals—Young adult (240 g-290 g) male Sprague-Dawley rats (Charles River, USA or Harlan, Israel) were used in the experiments.

(iii) Drugs—Nicotine (Sigma); opipramol (Rafa Laboratories Ltd. Jerusalem, Israel), McN-A-343 (4-(N-[3-chlorophenyl]-carbamoyloxy}-2-butynyl-trimethylammonium chloride—from R.B.I, USA), galantamine (Sigma, Israel), lidocaine (Sigma) and clomipramine (Sigma) were dissolved in 0.9% saline solution before use.

(iv) Determination of nicotine-induced hypothermia—Rats were placed individually in experimental cages kept at 25° C. and were allowed to rest for 1 h before drug injection. During this period, body temperature was measured at 15- or 30-min intervals in order to exclude the effect of handling on animal temperature. Body temperature was measured with a rectal thermistor probe (M.R.C, Israel, sensitivity 0.1° C.). The probe was lubricated with petroleum before being inserted into the rectum to a depth of 2 cm. The data are presented as changes in rectal temperature from the basal values. Basal values are those taken immediately before the drug injection (time 0).

(v) Elevated Platform Maze (EPM)—The purpose of the EPM is to determine the anxiolytic effects of tested drugs. The time that the experimental animals spend in the open arm of the maze is an indication for the anxiolytic effect, the longer the time the higher the anxiolytic effect. The EPM is a wooden, cross-shaped device, consisting of four arms arranged in the shape of a plus sign. Two of the arms have no side or end walls (open-arms; 30×5×0.25 cm). The other two arms have side walls and end walls, but are open on top (closed arms; 30×5×15 cm). The maze is elevated to a height of 50 cm. The animals are kept in a relatively dark box before exposure to the maze in order to increase their exploratory behavior. The tests were done in a silent environment under dim light. The animals were carried to the laboratory and left there undisturbed for 1 h before the experiment. Each rat was individually placed on the central platform 5×5 facing toward an open-arm and was observed for 5 min by two observers sitting in the same room, recording the time that the animals spent in the open arm.

(vi) Statistical analysis—The results are expressed as means±S.E.M of the data obtained from all the animals in each treatment group. The results were analyzed using ANOVA (α=0.05) or Student t-test when appropriate.

Example 1

Effect of Opipramol and MCN-A-343 on Nicotine-Induced Calcium Influx in Cultured Cells SK-N-SH human neuroblastoma cells, known to express nAChR, were grown in Dulbecco/Vogt Modified Eagle's Minimal Essential Medium (DMEM) to confluency in a 24-well plate. DMEM containing 45$Ca^{2+}$ without any other addition (1) or with 50 μM nicotine (2) or with 50 μM nicotine+10 μM opipramol (3) was added to cells grown in 24-well plates and preincubated with medium alone for 15 minutes, then washed rapidly. Intra cellular radioactivity was determined for each condition. The same medium with nicotine was added also to cells that were preincubated for 15 minutes with either 50 μM nicotine alone (4) or with 50 μM nicotine+10 μM opipramol (5). 45Ca2+ uptake was determined after 10 min. Activation of the nicotinic receptors causes calcium influx so it is a measure of the nicotinic receptor activity.

The results with opipramol are shown in FIG. 1. The first exposure to nicotine caused an increase in calcium influx (2) compared to basal uptake in the absence of nicotine (1). Simulation of the cells for the first time with nicotine in the presence of opipramol, also caused a significant rise in calcium uptake (3) which was only slightly smaller compared to that obtained with first stimulation with nicotine alone. However, when the cells were exposed to nicotine for the second time (4), calcium influx was considerably reduced due to nAChR receptor desensitization. By comparison, when the cells were stimulated with nicotine and opipramol during the first stimulation only a slight decrease in 45Ca2+ uptake was observed and in the second stimulation nAChR desensitization was remarkedly reduced (5), indicating that opipramol reduces receptor desensitization. DPM, disintegrations per minute. Similar results were obtained when 10 μM Mc-N-A-343 was used instead of opipramol (not shown).

Example 2

Figure 2:
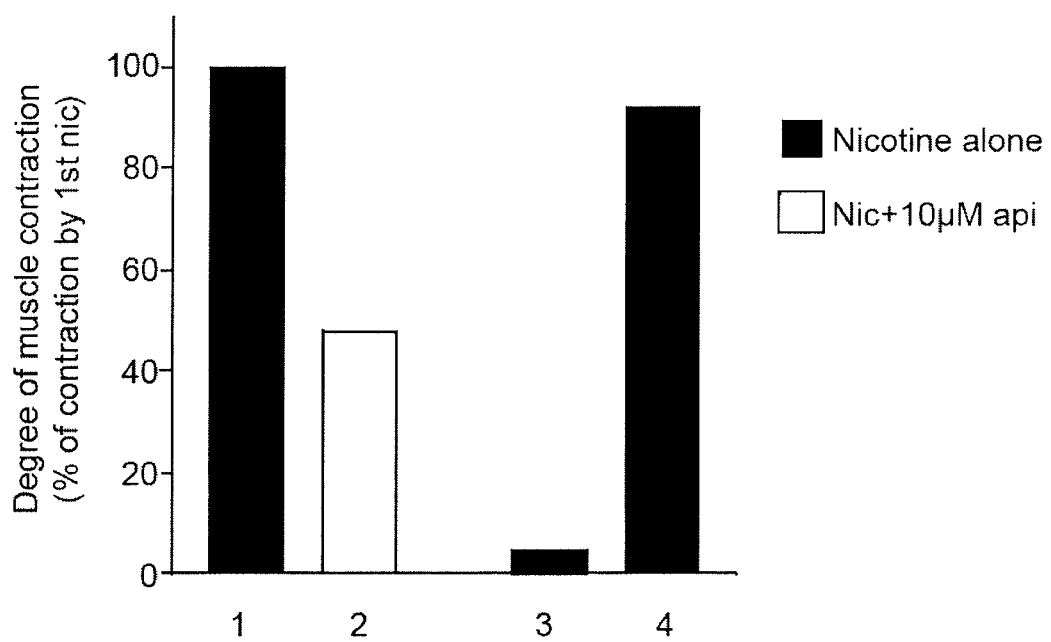
FIG. 2 depicts the effect of opipramol on nicotine-induced smooth muscle contraction using a Guinea pig ileum preparation experiment, where muscle contraction is shown as percent of contraction resulting from the addition of (1) 25 μM nicotine, (2) 25 μM nicotine in the presence of 10 μM opipramol, (3) as (1) but after the muscle was stimulated once with 25 μM nicotine; and (4) as (1) but after the muscle was stimulated once with 25 μM nicotine in the presence of 10 μM opipramol. Opi=opipramol, Nic=nicotine.

Effect of Opipramol on Nicotine-Induced Smooth Muscle Contraction and on Nicotine Induced Desensitization in the Guinea Pig Ileum Preparation The free end of a smooth muscle of a guinea pig ileum was attached to a force displacement transducer. Isometric tension of the smooth muscle was continuously monitored by outputting the preamplified transducer signal to a computer. Addition of 25 μM nicotine caused muscle contraction. The peak obtained with this concentration of nicotine was quantified by the displacement transducer and was normalized and defined as 100% contraction as shown in left black bar in FIG. 2 (1st stimulation; bar 1).

Opipramol reduced the effect of nicotine to about 50% of that induced by nicotine alone (1st stimulation; bar 2). The ileum preparation was washed by physiological solution 10 min after the addition of nicotine and then nicotine at a final concentration of 25 μM was added again to the muscle preparation for additional 10 min (2nd stimulation; bar 3). As can be seen, nicotine did not induce muscle contraction during the second stimulation (2nd stimulation; bar 4) due to receptor desensitization. However, if the first stimulation was done in the presence of opipramol (as described by bar 2 in the 1st stimulation), nicotine induced almost full response during the second stimulation (bar 4), indicating that opipramol prevented or reduced the nAChR desensitization.

When nicotine was administered together with opipramol the effect of nicotine was maintained steady for one hour until the removal of the drugs by washing (data not shown) indicating that opipramol effectively prevents nAChR desensitization.

Example 3

Effect of Opipramol on Nicotine-Induced Hypothermia in Rats

Figure 3A:
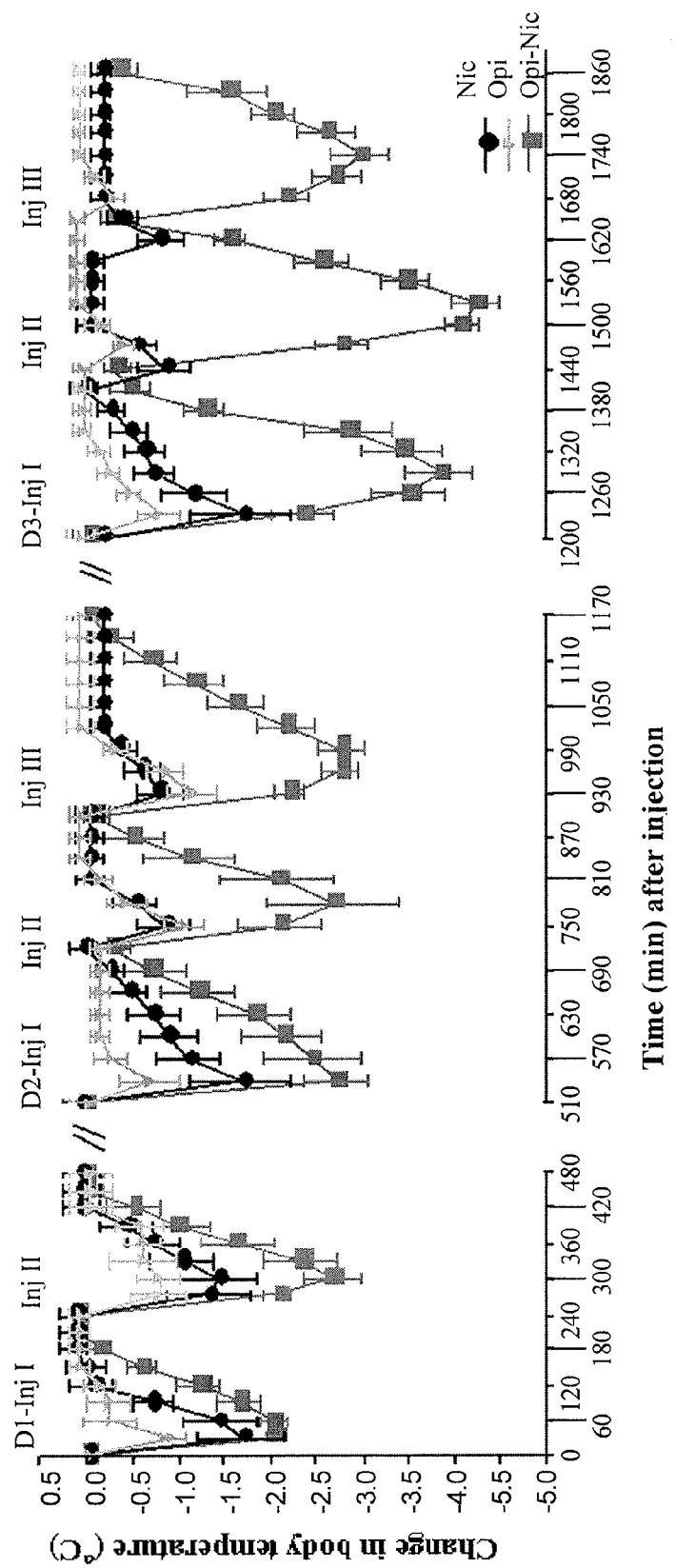
FIGS. 3A-3B depict the effect of 20 mg/kg opipramol on nicotine (2 mg/kg) induced hypothermia in rats.
Figure 3B:
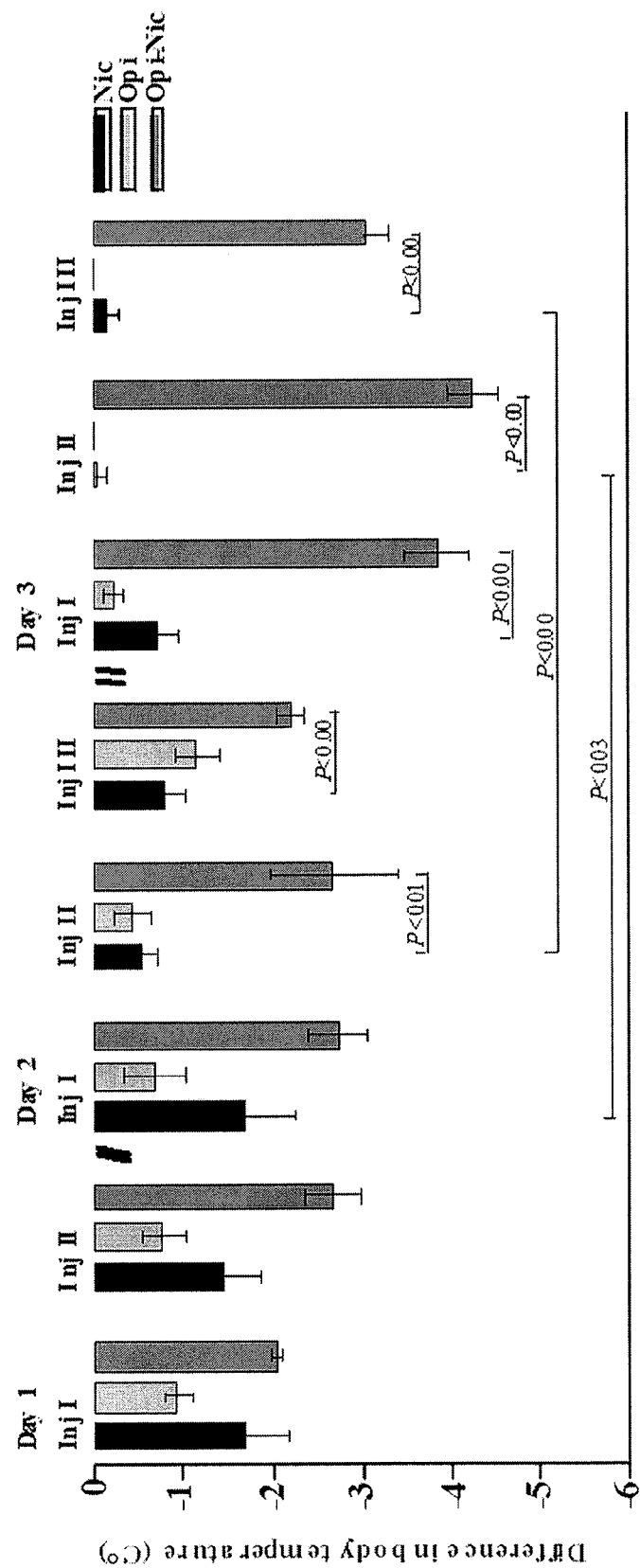

Rats were divided into three treatment groups, each of 5 rats, as follows: 1. treatment with nicotine (2 mg/kg); 2. treatment with opipramol (20 mg/kg); 3. treatment with opipramol (20 mg/kg) together with nicotine (2 mg/kg). Rats were injected with nicotine twice on the first day (FIG. 3A, D-1, left panel) and three times on days 2 (FIG. 3A, D-2, middle panel) and 3 (FIG. 3A, D-3, right panel). The intervals between the injections were 3 hours according to the time needed for returning to normal body temperature. Nicotine was injected with and without opipramol, and body temperature was measured at 30 min intervals. The results are shown in FIG. 3. (FIG. 3A: Filled circles—Rats injected with nicotine (2 mg/kg) three times a day in intervals of 3 hours for three consecutive days (N=5); Inversed triangles—Rats injected with opipramol (20 mg/kg) three times a day in intervals of 3 hours for three consecutive days (N=5); Filled squares—Rats injected with nicotine (2 mg/kg) and opipramol (20 mg/kg) three times a day in intervals of 3 hours for three consecutive days (N=5). D, day; Inj., Injection; Opi, opipramol; Nic, nicotine.) When nicotine (2 mg/kg) was repeatedly injected for three consecutive days, the magnitude of the decrease in body temperature induced by a constant dose of nicotine became progressively smaller (P<0.05), indicating desensitization of the nAChR. When opipramol was injected together with nicotine in the second and the third day, the magnitude of the reduction in body temperature was significantly larger than that induced by nicotine alone (P<0.001) after the second and the third injections. Opipramol alone caused only a slight decrease in body temperature. FIG. 3A: Each point is the Mean±S.E.M. of change in body temperature compared to the temperature measured at time 0 (before the first injection) for at least five rats. FIG. 3B depicts a bar histogram representing mean±S.E.M. of the maximum change in body temperature compared to the temperature measured just before the injection.

Example 4

Effect of Opipramol or Galantamine on Nicotine-Induced Hypothermia in Rats

Figure 4A:
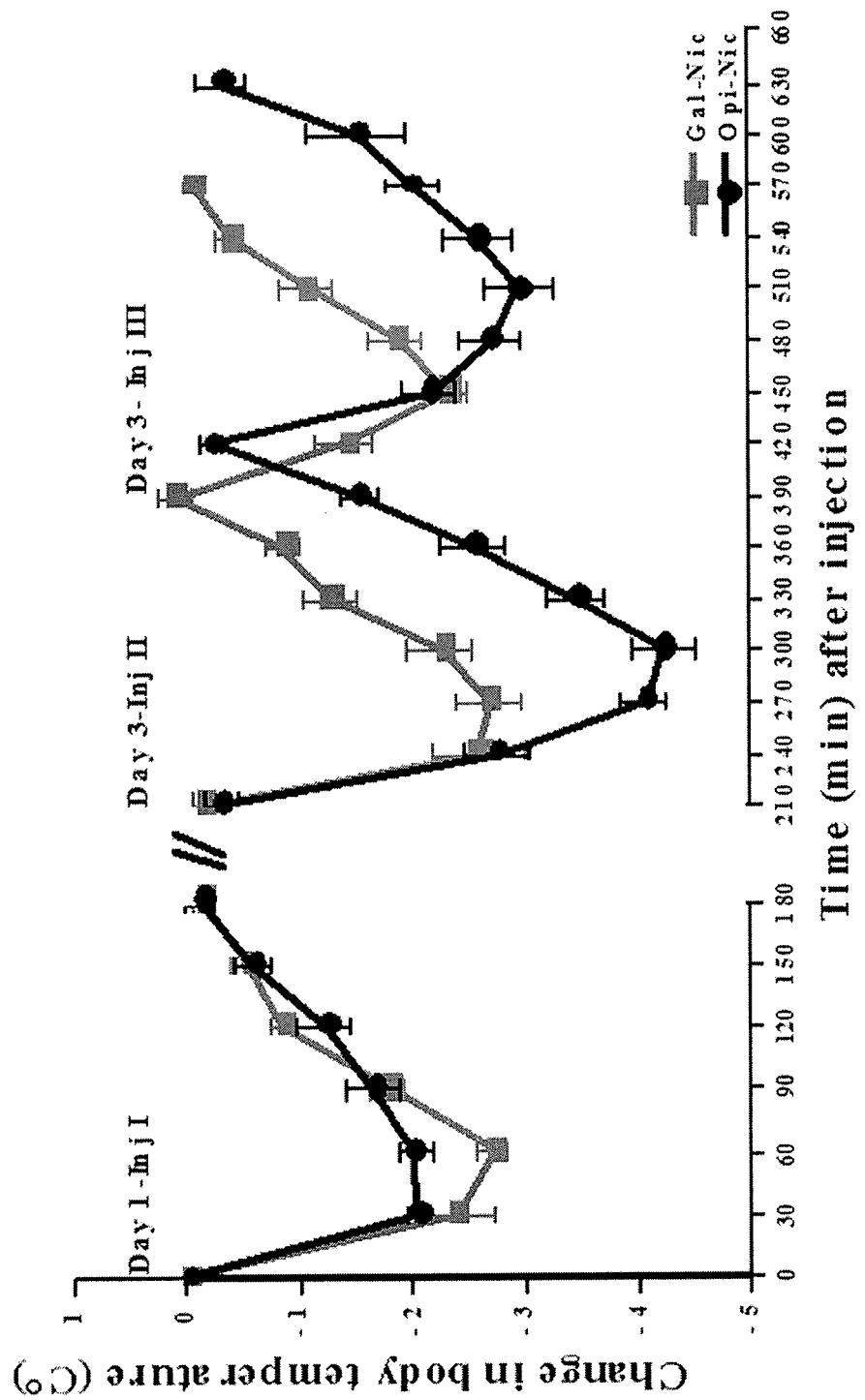
FIGS. 4A-4B depict the effect of opipramol (Opi) (20 mg/kg) or galantamine (Gal)(5 mg/kg) on nicotine (Nic) (2 mg/kg) induced hypothermia.
Figure 4B:
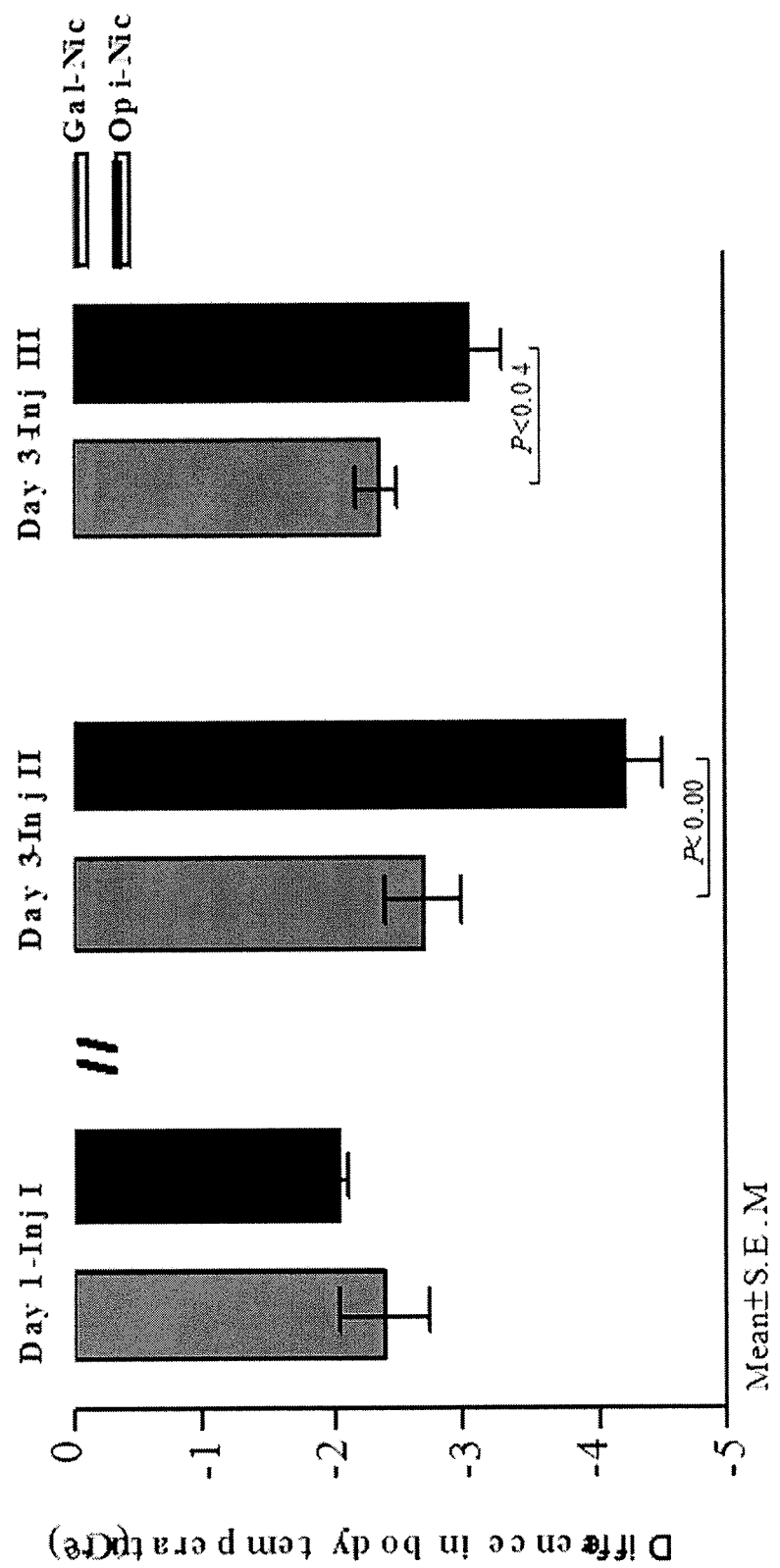

Following a similar protocol to that of Example 3, opipramol (20 mg/kg) or galantamine (5 mg/kg) were injected with and without nicotine. Body temperature was recorded at 30 min intervals. FIG. 4 depicts the results. FIG. 4A: Each point is the Mean±S.E.M. of change in body temperature compared to the temperature measured at time 0 (before the first injection) for at least five rats. 4B Bar histogram representing mean±S.E.M. of the maximum change in body temperature compared to the temperature measured just before the injection.

Example 5

Effect of Repeated Nicotine Administration on Anxiety in Rats

Figure 5A:
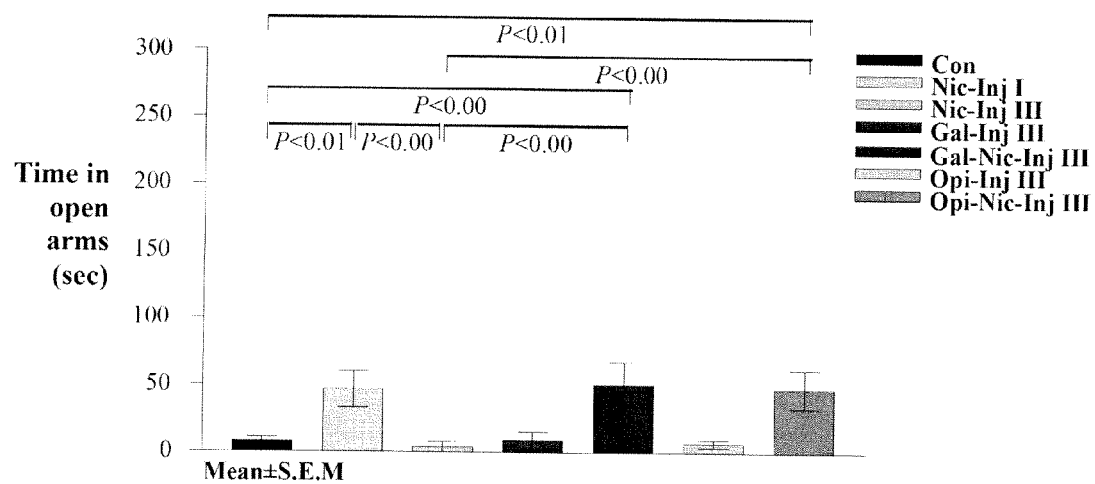
FIGS. 5A-C depict the effect of opipramol (10 mg/kg) or galantamine (5 mg/kg) with nicotine (0.5 mg/kg or 2 mg/kg) on anxiety in rats as assessed by their performance in an elevated plus maze. Bar histograms represent mean of time spent in open arms±S.E.M. 5A: Results of low dose of nicotine (0.5 mg/kg); 5B: Results of high dose of nicotine (2 mg/kg); 5C: Comparison between galantamine and opipramol with the low and high doses of nicotine.
Figure 5B:
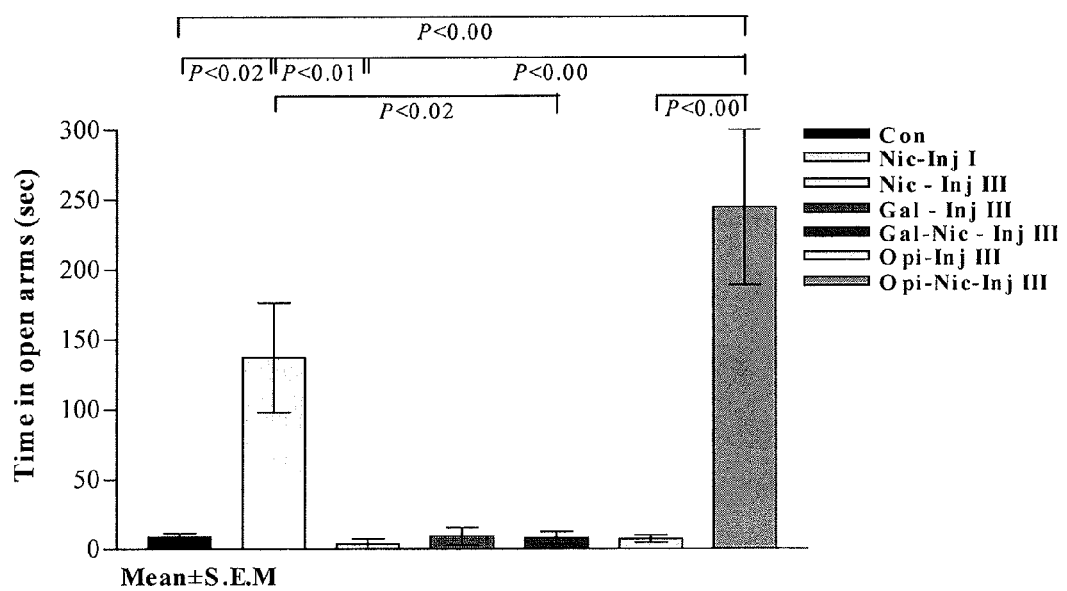
Figure 5C:
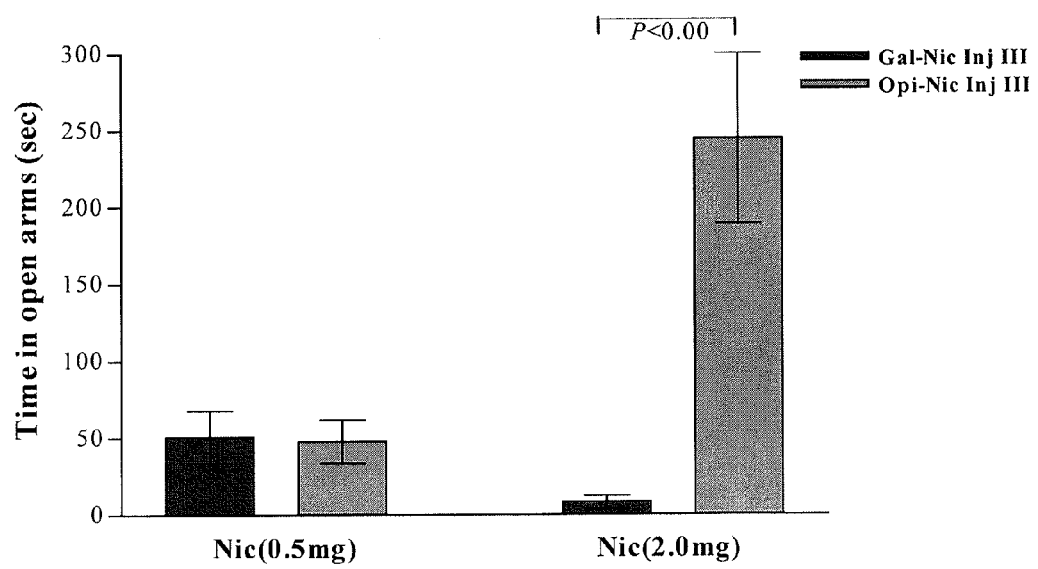

This test is used to assess anxiety. Rats were randomly assigned into five groups each containing 5 animals and then tested in an Elevated Plus Maze (EPM). In the first (control) group, rats were injected with saline once a day; in the second group rats were injected with nicotine (0.5 mg/kg or 2 mg/kg) three times a day and were tested in the maze after the third injection; in the third group rats were injected with opipramol (10 mg/kg) three times a day and then were tested in the maze; in the fourth group, rats were injected with opipramol (10 mg/kg) or galantamine (5 mg/kg), and nicotine (2 mg/kg or 0.5 mg/kg) three times a day and were tested in the maze after the last injection. The behavioral response to nicotine in the EPM was assessed 30 min after the first injection, and then again 30 minutes after the third injection. As can be seen from FIG. 5, one injection of nicotine significantly increased the time that the rats spent in the open arm, indicating the anxiolytic effect of nicotine. However, nicotine at both doses 0.5 mg/kg and 2 mg/kg did not induce an anxiolytic effect during the second injection due to receptor desensitization. When nicotine was injected together with either galantamine or opipramol, the anxiolytic effect was seen in the second injection (at 0.5 mg/kg nicotine), indicating that both galantamine and opipramol inhibited nAChR desensitization. Opipramol appears more effective in this test as it also inhibited desensitization when the dose of nicotine was raised to 2 mg/kg. Galantamine was not effective in inhibiting nAChR desensitization at this nicotine dose. Bar histograms represents mean of time spent in open arms±S.E.M. FIG. 5A depicts the results of low dose of nicotine (0.5 mg/kg), FIG. 5B depicts high dose of nicotine (2 mg/kg), FIG. 5C shows a comparison between galantamine and opipramol with different doses of nicotine.

Example 6

Effect of Nicotine and Opipramol on BDNF mRNA Expression in Rat Cortex

Nicotine alone (0.5 mg/kg) or opipramol (10 mg/kg) or nicotine (0.5 mg/kg)+opipramol (10 mg/kg) were injected intraperitoneally (ip) to rats (5 per group) at intervals of 2 hours during a single day. The drugs were dissolved in saline and used in the same day. Each injection had a volume of 1 ml/kg body weight. Animals were sacrificed 90 min after each injection and brain derived neurotrophic factor (BDNF) and β-actin mRNA were determined in homogenates of the cerebral cortex of each animal.

Homogenates of the cerebral cortex were prepared as follows: Rat brain tissues were sonicated for 15 sec and total RNA was obtained using the Trizol Reagent (Molecular Research Center, Cincinnati, Ohio, USA), according to the manufacturer's instructions. RNA concentrations were quantified by measuring the absorbances at 260 and 280 nm. RNA was reverse transcribed into cDNA during 45 min at 42° c. The cDNA products were diluted 1:40 for BDNF and 1:1000 for β-actin (a housekeeping gene for internal standard). In order to amplify gene specific sequences, PCR techniques were applied using ReadyMix PCR Master Mix (AB-genes, Surrey, UK) and specific primer sequences for BDNF and beta actin. The products were separated by electrophoresis on agarose and quantification of the bands was done by an image analyzer.

Figure 6:
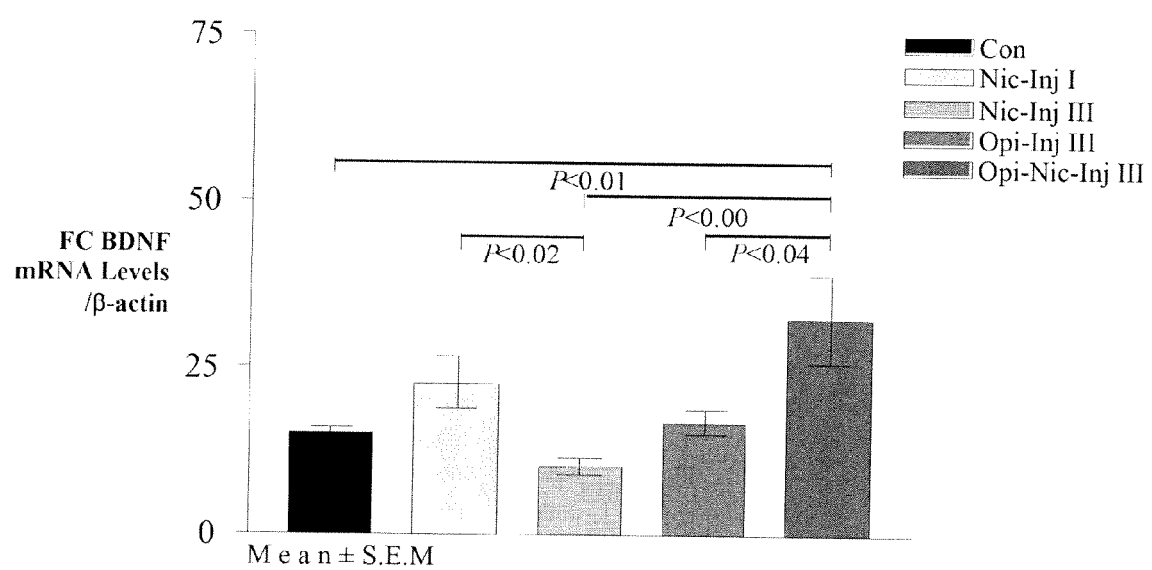
FIG. 6 depicts the effect of opipramol (10 mg/kg) and nicotine (0.5 mg/kg) on the expression of brain derived neurotrophic factor (BDNF) mRNA expression in rat cerebral cortex.

FIG. 6 depicts results (mean±SEM of the ratio of BDNF mRNA levels/β actin) of injections of a control (saline), nicotine alone (first and third injections), opipramol alone (third injection) and opipramol/nicotine injection (third injection). As can be seen, BDNF mRNA is increased as a result of treatment of the animals with nicotine. A repeated injection of nicotine was accompanied with a much smaller rise in BDNF mRNA as a result of nAChR desensitization. However, when nicotine was injected together with opipramol, the desensitization of the nAChR was inhibited and BDNF mRNA level was rising even above that which was observed with nicotine alone, indicating that opipramol can enhance the effect of nicotine and inhibit nAChR desensitization. Opipramol alone had no effect on the level of BDNF mRNA.

Example 7

Effect of Clomipramine on Nicotine-Induced Hypothermia in Rats

Figure 7:
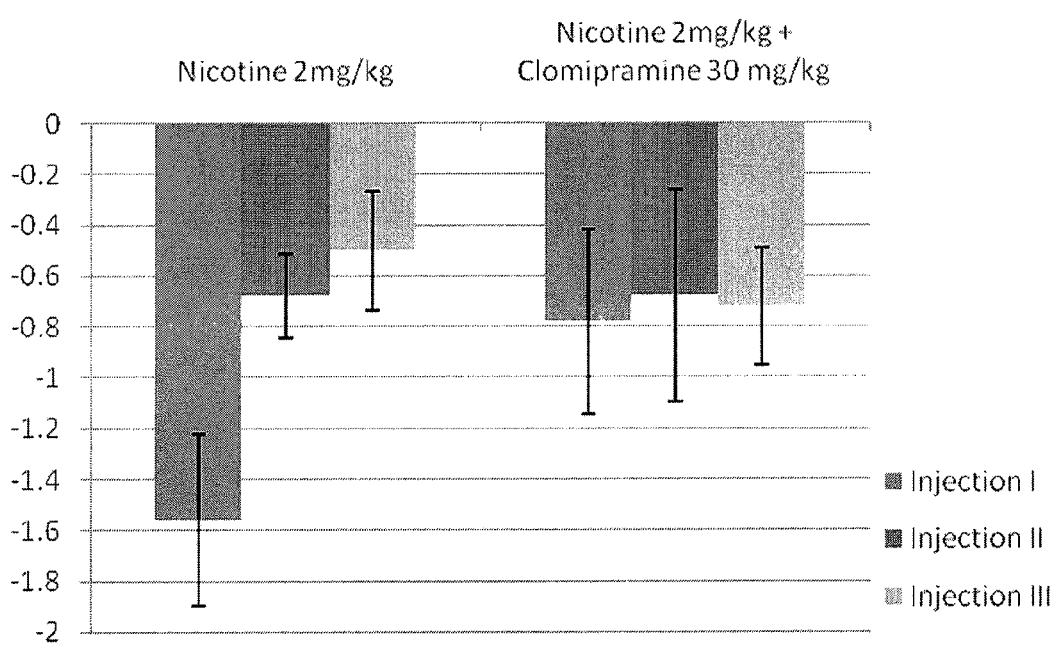
FIG. 7 depicts the effect of clomipramine (30 mg/kg) on nicotine-induced (2 mg/kg) hypothermia in rats.

Following a similar protocol to that of Example 3, nicotine (2 mg/kg) alone or in combination with clomipramine (30 mg/kg) was injected to rats 3 times, 2 h apart. The body temperature (0 C) was measured 30 min post injection. FIG. 7 depicts the maximum decrease in body temperature after each injection. As can be seen, when nicotine was injected alone, a gradual decrease in the hypothermic effect was seen, indicating nAChR desensitization. Clomipramine inhibited to some extent the effect of nicotine in the first injection, but no further reduction in the hypothermic effect of nicotine was noted in consecutive injections, suggesting that clomipramine inhibits nAChR desensitization.

Example 8

Effect of Lidocaine on Nicotine-Induced Hypothermia in Rats

Figure 8A:
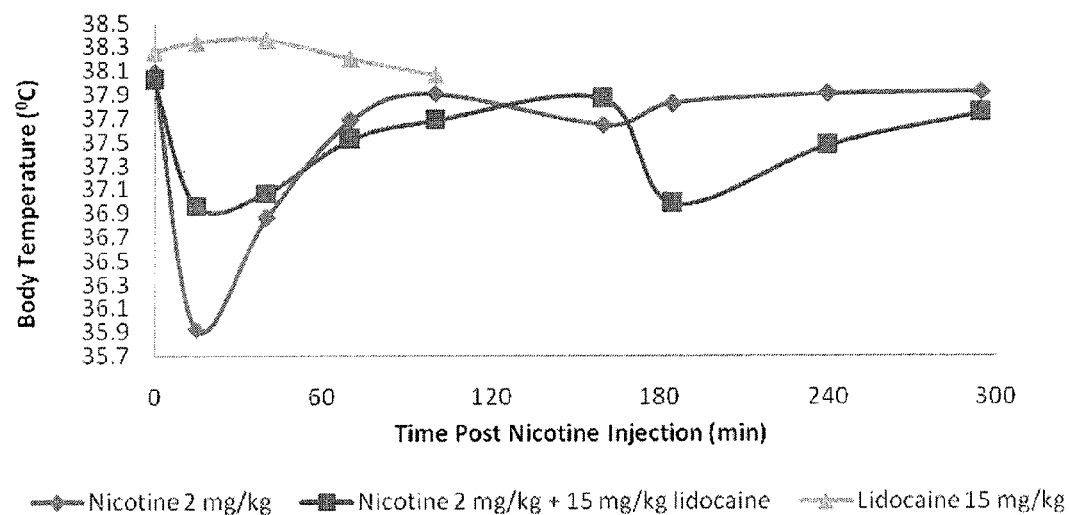
FIGS. 8A-B depicts the effect of lidocaine (15 mg/kg) on nicotine-(2 mg/kg) induced hypothermia in rats. The drugs were injected during two days (day 1 and day 2).
Figure 8B:
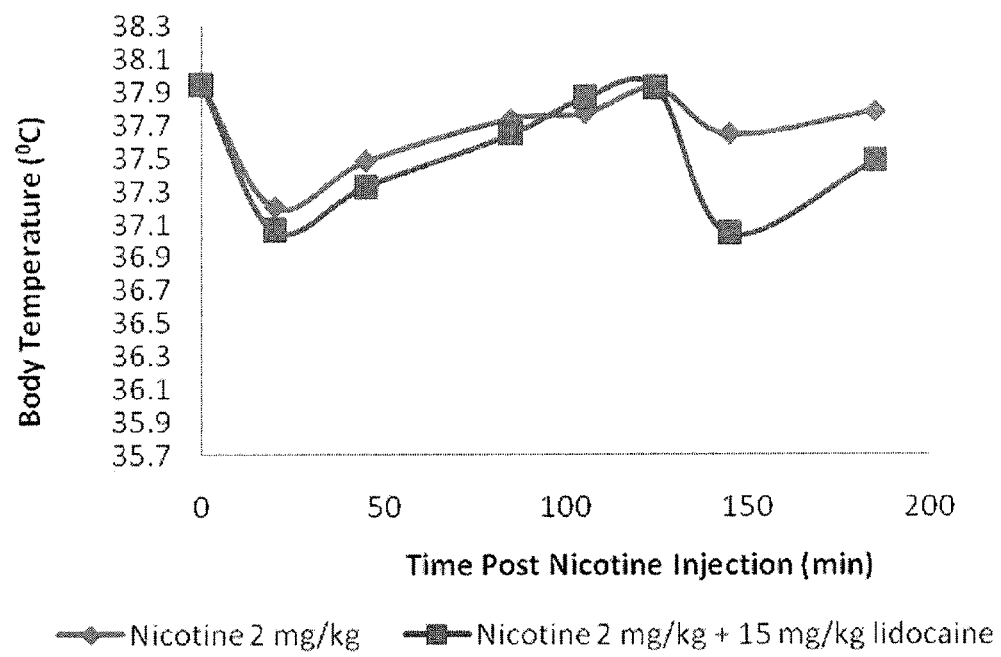

The experimental design was similar to that described in Example 3. Nicotine (2 mg/kg), lidocaine (15 mg/kg), and nicotine+lidocaine (2 mg/kg+15 mg/kg) were administered to rats 2× day for two days, following the above protocol. FIGS. 8A-8B depicts the results on day 1 and day 2, respectively, indicating that lidocaine maintained the hypothermic effect of nicotine compared to the loss of the hypothermic effect of nicotine when it was given alone. These results show that lidocaine inhibits nAChR desensitization.

The invention claimed is:

1. A method for treatment of attention deficit hyperactivity disorder (ADHD) or attention deficit disorder (ADD) comprising co-administering to a patient in need thereof a therapeutically effective amount of (a) nicotine, or a pharmaceutically acceptable salt or N-oxide thereof, and (b) opipramol, or a pharmaceutically acceptable salt or ester thereof.

2. The method of claim 1, wherein administration of a nicotinic agonist after said co-administration prolongs the duration of the nicotinic agonist effect by about a factor of two as compared to administering to the patient a nicotinic agonist alone.

3. The method of claim 1, wherein said opipramol reduces the desensitization of nicotinic acetylcholine receptors to said nicotine for at least about 12 hours.

4. The method of claim 1, wherein said nicotine and said opipramol are administered together in the same dosage form.

5. The method of claim 1, wherein said nicotine and said opipramol are administered in separate dosage forms.

6. The method of claim 1, wherein said nicotine and said opipramol, are each administered via a formulation chosen from: oral, parenteral, mucosal, inhalation and transdermal formulations, or a combination thereof.

7. The method of claim 1, wherein said nicotine is administered transdermally.

8. The method of claim 1, wherein said nicotine and said opipramol are administered in one transdermal patch.

9. The method of claim 1, wherein about 5 mg/day to about 21 mg/day of said nicotine is administered.

10. The method of claim 1, wherein said nicotine and said opipramol are present in a weight ratio of nicotine:opipramol of about 1:2 to about 1:100.

11. The method of claim 1, wherein said nicotine and said opipramol are present in a weight ratio of nicotine:opipramol of about 1:5 to about 1:20.

12. The method of claim 1, wherein said nicotine and said opipramol are present in a weight ratio of nicotine:opipramol of about 1:1.

13. A method for treatment of Alzheimer's disease comprising co-administering to a patient in need thereof a therapeutically effective amount of (a) nicotine, or a pharmaceutically acceptable salt or N-oxide thereof, and (b) opipramol, or a pharmaceutically acceptable salt or ester thereof.

14. A method for treatment of Parkinson's disease comprising co-administering to a patient in need thereof a therapeutically effective amount of (a) nicotine, or a pharmaceutically acceptable salt or N-oxide thereof, and (b) opipramol, or a pharmaceutically acceptable salt or ester thereof.

15. A method for treatment of ADHD comprising co-administering to a patient in need thereof a therapeutically effective amount of (a) nicotine, or a pharmaceutically acceptable salt or N-oxide thereof, and (b) opipramol, or a pharmaceutically acceptable salt or ester thereof.

16. A method for treatment of ADD comprising co-administering to a patient in need thereof a therapeutically effective amount of (a) nicotine, or a pharmaceutically acceptable salt or N-oxide thereof, and (b) opipramol, or a pharmaceutically acceptable salt or ester thereof.

* * * * *